United States Patent [19]

Millauer et al.

[11] 4,066,708
[45] Jan. 3, 1978

[54] PROCESS FOR PREPARING CHLORINATED HYDROQUINONE DIMETHYL ETHERS

[75] Inventors: Hans Millauer, Eschborn, Taunus; Rudolf Pistorius, Wehrheim, both of Germany

[73] Assignee: Hoechst Aktiengesellschaft, Frankfurt am Main, Germany

[21] Appl. No.: 723,486

[22] Filed: Sept. 15, 1976

[51] Int. Cl.$^2$ ............................................ C07C 41/00
[52] U.S. Cl. ............................................... 260/613 D
[58] Field of Search .................................. 260/613 D

[56] References Cited

PUBLICATIONS

Weinberg et al., J.A.C.S., vol. 85, (1963), pp. 2525–2526.

Primary Examiner—Bernard Helfin
Attorney, Agent, or Firm—Curtis, Morris & Safford

[57] ABSTRACT

Chlorinated hydroquinone dimethyl ethers of the formula

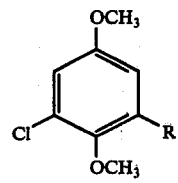

wherein R is H or Cl are prepared by reacting p-benzoquinone tetramethyl diketals of the formula

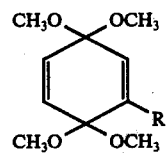

wherein R is defined as above, with an excess of hydrogen chloride in an aprotic solvent at a temperature from about −50° to +50° C. The products I are valuable intermediates for the preparation of dyestuffs, insecticides and pharmaceutics.

7 Claims, No Drawings

PROCESS FOR PREPARING CHLORINATED HYDROQUINONE DIMETHYL ETHERS

The present invention relates to chlorinated hydroquinone dimethyl ethers of the formula

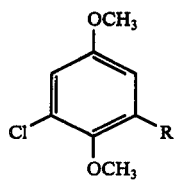

wherein R is hydrogen or chlorine.

Chlorinated hydroquinone dimethyl ethers of the above formula are valuable intermediates for the preparation of dyestuffs, insecticides and pharmaceutics. Hydroquinone dimethyl ethers in their turn may be prepared by known methods from the corresponding hydroquinone starting compounds.

The technically important chlorohydroquinone dimethyl ether, the compound of the formula I wherein R is H, for example, may be prepared by direct chlorination of hydroquinone dimethyl ether according to H. E. Akerman et al, J.Appl.Chem. 3, 416 (1953). When performing the process in practice, there is always formed a considerable quantity of the disubstitution product 2,5-dichloro-hydroquinone dimethyl ether.

By the use of the chlorination agent sulfuryl chloride instead of chlorine (cf. Houben-Weyl, Methoden der Organischen Chemie, fourth edition, volume 5,3 pages 883 – 884, editor Georg Thieme, Stuttgart 1962), the prior processes are not essentially improved.

(Mono)chloro-hydroquinone dimethyl ether may also be obtained by methylation of chlorohydroquinone with dimethyl sulfate according to Posternak et al.

According to U.S. Pat. No. 1,919,580 aminohydroquinone dimethyl ether is used as starting compound, which is converted into chlorohydroquinone dimethyl ether by the reaction according to Sandmeyer.

2,6-Dichloro-hydroquinone dimethyl ether, the compound of the formula I wherein R is Cl, is obtained by methylation of the corresponding 2,6-dichlorohydroquinone, which can only be prepared with difficulties (cf. M. Kohn and R. Marberger, Monatshefte fur Chemie 45, 654 [1924]; M. Kohn and J. Sussmann. Monatshefte fur Chemie 48, 199 [1927]).

In all cited processes there are used as starting compounds for the preparation of the chlorinated hydroquinone dimethyl ethers hydroquinone compounds, which are generally obtained from the corresponding quinoid compounds or from quinones; the latter in their turn may be obtained by oxidation of benzenic compounds. The industrial preparation of chloro-hydroquinone dimethyl ether illustrates the cited mode of preparation especially clearly; aniline is used as starting material, which is oxidized to p-benzoquinone by means of manganese dioxide, quinone is reduced to hydroquinone by means of sulfurous acid, which hydroquinone is then methylated with methyl chloride and finally chlorinated.

It was therefore desirable to find a simpler process for the preparation of chlorinated hydroquinone dimethyl ethers, especially of monochloro-hydroquinone dimethyl ethers to be carried out in an easier manner on an industrial scale.

This problem has been solved by the present invention by using as starting compounds p-benzoquinone tetramethyl ketals of the formula II

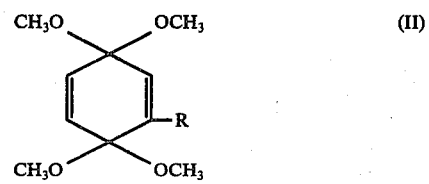

wherein R is hydrogen or chlorine, by mixing said ketals with a solution of excess hydrogen chlorine in an aprotic solvent at a temperature from about $-50°$ to $+50°$ C and isolating the products formed of the formula I in known manner.

The reaction formally takes place in one step according to the reaction equation

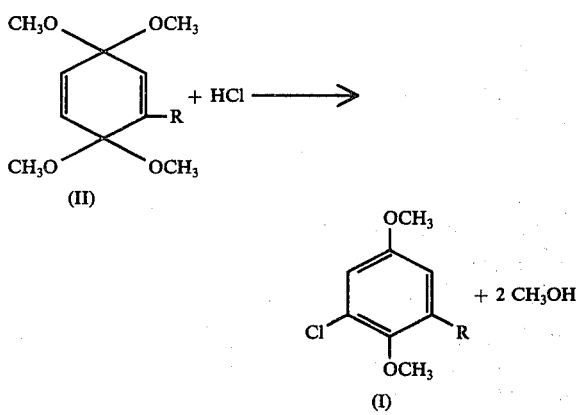

p-Benzoquinone diketals of the formula II have been produced electrochemically for the first time as a result of the studies of N. L. Weinberg and B. Belleau, J.Am.-Chem.Soc. 85, 2525 (1963). According to said reference p-benzoquinone tetramethyl ketal of the formula II wherein R is hydrogen, for example is prepared by anodic oxidation of anisol or of hydroquinone dimethyl ether in methanol/HOH. Unsubstituted benzene cannot be used as starting compound for this reaction. According to the process disclosed in German Offenlegungsschrift No. 2,460,754, however it may also be used. According to this process benzene, anisol or anisol substituted in ortho or meta position is oxidized anodically in a methanolic solution in the presence of at least one ammonium or alkali metal fluoride, perchlorate, nitrate, tetrafluoroborate, hexafluorosilicate, hexafluorophosphate or p-toluenesulfonate as conducting salt as well as of optionally a difficultly oxidizable base such as 2,6-lutidine, at a pH from 7 to about 10 at a known anode made from graphite, a metal selected from the group of platinum or its alloys or from PbO$_2$; the temperature is in the range from about $-20°$ to $+60°$ C. This process permits preparing the unsubstituted p-benzoquinone tetramethyl-ketal from benzene and anisol as starting material, or chloro-p-benzoquinone tetramethyl ketal from o- or m-chloroanisol as starting material.

The unsubstituted p-benzoquinone tetramethyl ketal or the monochloro-p-benzoquinone tetramethyl ketal are advantageously mixed while stirring with a solution of excess hydrogen chloride in an aprotic solvent, at a temperature from about $-50°$ to $+50°$ C, preferably from about −40° to +30° C, especially from about −20° to +20° C.

Mixing is advantageously performed by adding tetramethylketal to the solution of excess hydrogen chloride in the chosen aprotic solvent. It is moreover advantageous to use tetramethyl ketal likewise in a dissolved state, advantageously in the same solvent, in which hydrogen chloride is dissolved. The process may be carried out in any usual flask provided with a stirrer made from glass or in enamelled vessels provided with a stirrer. The excess of hydrogen chloride, calculated on the quantity of p-benzoquinone tetramethyl ketal may vary within rather wide limits. The process may be carried out with a molar quantity of hydrogen chloride amounting to about 1.2 to 20 times, preferably to about 1.5 to 10 times, the quantity of p-benzoquinone tetramethyl ketal used. After combination of the reactants the reaction mixture is advantageously stirred for a period from about half an hour to 1 hour.

Suitable aprotic solvents are those selected from the group of ethers such as diethyl ethers, diisopropyl ethers, glycol dimethyl ethers, diethylene glycol dimethyl ethers, dioxan etc., as well as acetonitrile, dimethyl formamide, benzene, methylene chloride, chloroform etc. Highly polar aprotic solvents selected from the group of ethers and especially diethyl ethers and dioxane are used preferably, benzene is moreover used preferably. The solvent should be used in an anhydrous state. When dissolving hydrogen chloride care must be taken that no water or only traces of water are introduced into the solution.

The concentration of the reactants in the solvent used may vary from about 5 to 50% by weight or go even up to saturation in accordance with the reaction temperature used, a concentration from about 10 to 25% by weight being preferred.

When the reaction of p-benzoquinone tetramethyl ketal II and hydrogen chloride is finished the products of the invention are separated from the reaction mixture in known manner, for example by removing the excess of hydrogen chloride and of the methanol formed by washing with water or with aqueous alkalis, by separation and drying of the organic phase and by subsequent distillative separation of the remaining solvent. Solvents miscible with water may be separated completely or partially by washing in such a way. It is likewise possible, however, to separate by distillation the methanol formed and the solvent.

The crude products remaining after removal of the solvent have a purity from about 90 to 98%. A further purification may be performed for example by fractional distillation or by redissolving. It is very surprising that the process of the invention can be performed with high yields owing to the fact that p-benzoquinone diketals are compounds which are highly sensitive to acids and react under the action of Lewis acids, for example to form a variety of different substances. (Cf. G. Buchanan et al., J.Am.Chem.Soc. Peskin Transact I, 1973, 373 – 75). p-Benzoquinone diketals moreover decompose under the action of even very small quantities of strong acids, for example $H_2SO_4$ or $HBF_4$ practically instantaneously to form dark-colored and undefined product mixtures.

The reaction according to the invention is very specific and cannot be transferred to analogous starting compounds at least under the same conditions or only to a limited degree as the yields would not be at all as good as in the process of the invention.

The following Examples illustrate the invention:

EXAMPLE 1

A solution of 18.2 g (0.5 mol) of hydrogen chloride in 80 ml of diethyl ether is introduced into a 250 ml flask provided with a stirrer, a thermometer, a reflux condenser and a dropping funnel. 10.0 g (0.05 mol) of p-benzoquinone tetramethyl ketal dissolved in 20 ml of diethyl ether are added dropwise while stirring and cooling by means of ice water at +10° C and the reaction mixture is stirred for one hour at a temperature from about +10° to +15° C.

The reaction mixture is then extracted twice with 100 ml of water and once with 100 ml of a 5% solution of sodium dicarbonate and concentrated in a rotary evaporator at 50° C/10 torrs.

The distillation residue is composed at 7.5 g of crude product containing 98.2% of chloro-1,4-dimethoxybenzene according to the gaschromatographic analysis, which corresponds to a yield of about 87% of the theory calculated on p-benzoquinone tetramethyl ketal used.

EXAMPLE 2

Example 1, is repeated except that 1,4-dioxane is used as a solvent instead of diethyl ether.

7.3 g of crude product are obtained containing 97% of chloro-1,4-dimethoxybenzene according to the gaschromatographic analysis, which corresponds to yield of about 85% of the theory, calculated on p-benzoquinone tetramethyl ketal used.

EXAMPLE 3

The example is performed as Example 1, except that 1,2-dimethoxyethane is used as a solvent instead of diethyl ether.

7.8 g of crude product are obtained containing 97.1% of chloro-1,4-dimethoxybenzene according to the analysis by gas chromatography, which corresponds to a yield of the theory of about 90%, calculated on p-benzoquinone tetramethyl ketals used.

EXAMPLE 4

A solution of 10.9 g (0.30 mol) of hydrogen chloride in 100 g of 1,2-dimethoxyethane is introduced into a 250 ml flask provided with a stirrer, a thermometer, a reflux condenser and a dropping funnel. 40.0 g (0.20 mol) of p-benzoquinone tetramethyl ketal dissolved in 75 ml of 1,2-dimethoxyethane are added dropwise while stirring and cooling with ice water at a temperature from +5° to +10° C within 45 minutes. The reaction mixture is then stirred for 2 hours at a temperature from +20° to +25° C.

After extraction with 200 ml of water the organic phase is separated and the aqueous phase is extracted once with 50 ml of methylene chloride. The organic phases are combined, washed with 150 ml of a 2% solution of sodium hydrogenocarbonate and concentrated at a rotation evaporator at 50° C under a pressure of 10 torrs.

The distillation residue is composed of 33.7% of crude product which contains 95.7% of chloro-1,4-dimethoxybenzene according to the gaschromatographic analysis, which corresponds to a yield of about 93% of the theory, calculated on p-benzoquinone tetramethyl ketal used.

EXAMPLE 5

A solution of 18.2 g (0.5 mol) of hydrogen chloride in 100 g of 1,2-dimethoxyethane is changed into a 500 ml flask provided with a stirrer, a thermometer, a reflux condenser and a dropping funnel. 23.0 g (0.1 mol) of chloro-p-benzoquinone tetramethyl ketal dissolved in 50 ml of 1,2-dimethoxyethane are added dropwise while stirring and cooling with ice water at a temperature from +15° to +20° C within 15 minutes. Thereafter the reaction mixture is stirred for 4 hours at a temperature from 20° to 25° C.

For working up the reaction mixture is extracted with 400 ml of water, washed subsequently with 100 ml of a 2% solution of sodium hydrogeno-carbonate and concentrated at a rotation evaporator at a temperature of 50° C/10 torrs.

The distillation residue is composed of 19.35 g of crude product containing 78.5% of 2,6-dichloro-1,4-dimethoxybenzene according to the gaschromatographic analysis, which corresponds to a yield of about 76% of the theory, calculated on chloro-p-benzoquinone tetramethyl ketal used.

EXAMPLE 6

A solution of 16 g (0.43 mol) of hydrogen chloride in 500 g of benzene is introduced into a 1 liter flask provided with a stirrer, a thermometer, a reflux condenser and a dropping funnel.

20.0 g (0.10 mol) of p-benzoquinone tetramethyl ketal dissolved in 25 ml of benzene are added dropwise while stirring and cooling with ice water within 15 minutes. The reaction mixture is then stirred for 2 hours at a temperature from +20° to 25° C.

The reaction mixture is extracted with 200 ml of water, the benzenic phase is separated, washed with 100 ml of a 2% solution of sodium hydrogenocarbonate and concentrated in a rotary evaporator at 50° C/10 torrs.

The distillation residue is composed of 15.8 g of crude product containing about 93% of chloro-1,4-dimethoxybenzene, about 6% of benzene and about 1% of further substances according to the gaschromatographic analysis, which corresponds to a yield of about 86% of the theory, calculated on p-benzoquinone tetramethyl ketal used.

What is claimed is:

1. A process for preparing chlorinated hydroquinone dimethyl ethers of the formula

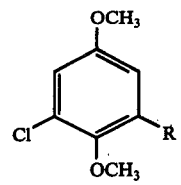

wherein R is hydrogen or chlorine, from quinoid starting compounds which comprises mixing p-benzoquinone tetramethyl diketals of the formula

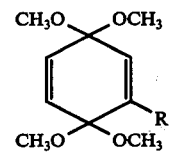

wherein R is defined as in the formula I, with a solution of an excess of hydrogen chloride in an aprotic solvent, at a temperature from about −50° to +50° C and isolating the products of the formula I thus formed.

2. Process as claimed in claim 1, wherein the temperature during mixing is in the range from about −50° to +30° C.

3. Process as claimed in claim 1, wherein the temperature during mixing is in the range from about −20° to +20° C.

4. Process as claimed in claim 1, which comprises mixing the reactants by adding p-benzoquinone tetramethyl ketal of the formula II to the solution of excess hydrogen chloride in an aprotic solvent.

5. Process as claimed in claim 1, which comprises dissolving p-benzoquinone tetramethyl ketal of the formula II prior to mixing in the same solvent as is used for the hydrogen chloride.

6. Process as claimed in claim 5, which comprises using an ether as the aprotic solvent.

7. Process as claimed in claim 1, which comprises using as an aprotic solvent diethyl ether, dioxane or benzene.